US011276494B2

(12) United States Patent
Zhang et al.

(10) Patent No.: US 11,276,494 B2
(45) Date of Patent: Mar. 15, 2022

(54) PREDICTING INTERACTIONS BETWEEN DRUGS AND DISEASES

(71) Applicant: INTERNATIONAL BUSINESS MACHINES CORPORATION, Armonk, NY (US)

(72) Inventors: Ping Zhang, White Plains, NY (US); Achille B Fokoue-Nkoutche, White Plains, NY (US); Sanjoy Dey, White Plains, NY (US); Katherine Shen, New York, NY (US)

(73) Assignee: International Business Machines Corporation, Armonk, NY (US)

( * ) Notice: Subject to any disclaimer, the term of this patent is extended or adjusted under 35 U.S.C. 154(b) by 357 days.

(21) Appl. No.: 15/976,970

(22) Filed: May 11, 2018

(65) Prior Publication Data

US 2019/0348179 A1 Nov. 14, 2019

(51) Int. Cl.
*G16H 50/20* (2018.01)
*G16H 70/40* (2018.01)
*G06N 20/00* (2019.01)

(52) U.S. Cl.
CPC ............. *G16H 50/20* (2018.01); *G06N 20/00* (2019.01); *G16H 70/40* (2018.01)

(58) Field of Classification Search
CPC ................... G06Q 50/22–24; G06Q 50/20–26
See application file for complete search history.

(56) References Cited

U.S. PATENT DOCUMENTS

| 2006/0179050 | A1* | 8/2006 | Giang | G06F 16/3346 |
| 2009/0024615 | A1* | 1/2009 | Pedro | G06F 16/367 |
| 2011/0276344 | A1* | 11/2011 | Williams | G16H 50/20 |
| | | | | 705/2 |

(Continued)

FOREIGN PATENT DOCUMENTS

| CN | 105653846 A | 6/2016 |
| CN | 107391927 A | 11/2017 |
| KR | 101450784 B1 | 10/2014 |

OTHER PUBLICATIONS

Hulisz et al., "Food-Drug Interactions" U.S. Pharmacist (Year: 2007).*

(Continued)

*Primary Examiner* — Neal Sereboff
(74) *Attorney, Agent, or Firm* — Kristofer L. Haggerty

(57) ABSTRACT

Embodiments of the present invention disclose a method, a computer program product, and a computer system for predicting drug and disease interactions. A computer identifies one or more drug similarity measures between one or more drugs and one or more disease similarity measures between one or more diseases. In addition, the computer identifies one or more interactions between the one or more drugs and the one or more diseases, then calculates one or more drug-disease feature vectors based on the one or more interactions, the one or more drug similarity measures, and the one or more disease similarity measures. Furthermore, the computer calculates a first probability indicating whether a first drug of the one or more drugs will interact with a first disease of the one or more diseases based on a model, wherein the model is trained based on the one or more drug-disease feature vectors.

8 Claims, 6 Drawing Sheets

(56) References Cited

U.S. PATENT DOCUMENTS

| | | | | |
|---|---|---|---|---|
| 2011/0295621 | A1* | 12/2011 | Farooq | G16H 10/60 705/3 |
| 2013/0179375 | A1* | 7/2013 | Tatonetti | G16H 50/50 706/12 |
| 2014/0337306 | A1* | 11/2014 | Gramatica | G06F 16/2471 707/706 |
| 2015/0036138 | A1* | 2/2015 | Watson | G01N 21/31 356/402 |
| 2016/0140327 | A1* | 5/2016 | Hu | G16C 20/30 702/30 |
| 2016/0171383 | A1 | 6/2016 | Narain et al. | |
| 2016/0232309 | A1 | 8/2016 | Yoon et al. | |
| 2017/0004277 | A1* | 1/2017 | Manczinger | G16H 50/50 |
| 2017/0270254 | A1 | 9/2017 | Guney et al. | |
| 2019/0035494 | A1* | 1/2019 | Zhang | G16H 70/40 |

OTHER PUBLICATIONS

Patel et al., "MeSHDD: Literature-based drug-drug similarity for drug repositioning" Journal of the American Medical Informatics Association, 24(3), 2017, 614-618 (Year: 2016).*

Karabulut, Nermin, "A drug similarity network for understanding drug mechanism of action" Journal of Bioinformatics and Computational Biology vol. 12, No. 2 (2014) 1441007 (Year: 2014).*

Schrader, "What's the Difference between an ontology and a knowledge graph?" As downloaded from https://appserver-5d00cb11-nginx-53c963b6d0f34506a0d08363c882d85f:14429/whats-the-di¶erence-between-an-ontology-and-a-knowledge-graph/ (Year: 2020).*

Onotext, "What is a knowledge graph?" As downloaded from https://www.ontotext.com/knowledgehub/fundamentals/what-is-a-knowledge-graph/#:~:text=The%20knowledge%20graph%20represents%20a,%2C%20unification%2C%20analytics%20and%20sharing. (Year: 2020).*

Mathur et al., "Finding disease similarity based on implicit semantic similarity" 1532-0464/$—see front matter 2011 Elsevier Inc. All rights reserved. doi:10.1016/j.jbi.2011.11.017 (Year: 2011).*

Manchanda et al., "Representation learning of drug and disease terms for drug repositioning" Cite as: arXiv:1705.05183 [cs.CL] ( Year: 2017).*

Luo et al., "DDI-CPI, a server that predicts drug-drug interactions through implementing the chemical-protein interactome" W46-W52 Nucleic Acids Research, 2014, vol. 42, Web Server issue doi: 10.1093/nar/gku433 (Year: 2014).*

Zitnik et al., "Collective Pairwise Classification for Multi-Way Analysis of Disease and Drug Data", HHS Public Access, Pac Symp Biocomput, 2016: 21: 81-92.

Zhang et al., "Predicting Drug-Disease Associations Based on the Known Association Bipartite Network", 2017 IEEE International Conference on Bioinformatics and Biomedicine (BIBM), pp. 497-503.

Jeon et al., "BEReX: Biomedical Entity-Relationship eXplorer", Bioinformatics, vol. 30, No. 1 2014, pp. 135-136.

Haslam et al., "Learning Disease Relationships From Clinical Drug Trials", Journal of the American Medical Informatics Association Advance Access published May 17, 2016, pp. 1-11.

Wu et al., "Predicting Drug-Disease Interactions by Semi-Supervised Graph Cut Algorithm and Three-Layer Data Integration", IEEE BIBM International Conference on Bioinformatics & Biomedicine (BIBM) 2016, pp. 1-14.

Lindblad et al., "Clinically Important Drug-Disease Interactions and Their Prevalence in Older Adults", Clinical Therapeutics, vol. 28, No. 8, Aug. 2006, pp. 1133-1143.

Dumbreck et al., "Drug-disease and drug-drug interactions: systematic examination of recommendations in 12 UK national clinical guidelines", the bmj | BMJ 2015;350:h949 | doi: 10.1136/bmj.h949, Jan. 12, 2015, pp. 1-8.

Gnjidic et al., "Clinical Implicatons from Drug-Drug and Drug-Disease Interactions in Older People", Clinical and Experimental Pharmacology and Physiology (2013) 40, pp. 320-325.

Zhan et al., "Suboptimal Prescribing in Elderly Outpatients: Potentially Harmful Drug-Drug and Drug-Disease Combinations", 2005 by the American Geriatrics Society, pp. 1-6.

Mell et al., "The NIST Definition of Cloud Computing", National Institute of Standards and Technology, Special Publication 800-145, Sep. 2011, pp. 1-7.

* cited by examiner

PREDICTING INTERACTIONS BETWEEN DRUGS AND DISEASES

BACKGROUND

The present invention relates generally to data analytics, and more particularly to predicting interactions between drugs and diseases.

Drug-disease interactions occur when an ingested drug worsens or exacerbates an existing medical condition or disease. For example, patients having high blood pressure who ingest nicotine may experience an increased heart rate, while asthmatic patients taking nonsteroidal anti-inflammatory drugs (NSAID) may experience air way obstruction. Moreover, particular diseases such as diabetes, high/low blood pressure, ulcers, glaucoma, enlarged prostate, poor bladder control, and insomnia are disease known to be more likely to cause a drug-disease interaction. The relationships, and more specifically interactions between drugs and diseases, are gaining increasing recognition in healthcare and medical fields as a concern that need be addressed. Moreover, identifying such interactions beforehand can reduce and possibly prevent the future occurrences of unexpected drug-disease interactions.

SUMMARY

Embodiments of the present invention disclose a method, a computer program product, and a computer system for predicting drug and disease interactions. A computer identifies one or more drug similarity measures between one or more drugs and one or more disease similarity measures between one or more diseases. In addition, the computer identifies one or more interactions between the one or more drugs and the one or more diseases, then calculates one or more drug-disease feature vectors based on the one or more interactions, the one or more drug similarity measures, and the one or more disease similarity measures. Furthermore, the computer calculates a first probability indicating whether a first drug of the one or more drugs will interact with a first disease of the one or more diseases based on a model, wherein the model is trained based on the one or more drug-disease feature vectors.

In embodiments, the method may further comprise identifying, based on determining that the first probability exceeds a threshold, a second drug having a same intended result of the first drug, and determining a second probability indicating whether the second drug will interact with the first disease. In further embodiments, the method may further comprise utilizing the first probability in a causality assessment.

According to embodiments of the present invention, the model utilizes the one or more interactions as training data, and the one or more drug similarity measures and the one or more disease similarity measures as variables that are deterministic of the first probability. In various embodiments of the method, the model is trained based on logistic regression.

Moreover, in various embodiments of the present application, the one or more drug similarity measures include measures selected from the group comprising chemical structure, drug target, chemical-protein interactome profile, mechanism of action, anatomical therapeutic chemical, metabolizing enzyme, medical subject headings category, side effect, physiological effect, and pathway. Similarly, the one or more disease similarity measures include measures selected from the group comprising semantic, disease ontology, disease gene, disease phenotype, disease symptom, disease comorbidity, disease pathology, disease morphology, application independent, domain specific, process based, molecular, and cellular.

BRIEF DESCRIPTION OF THE SEVERAL VIEWS OF THE DRAWINGS

The following detailed description, given by way of example and not intended to limit the invention solely thereto, will best be appreciated in conjunction with the accompanying drawings, in which.

The drawings are not necessarily to scale. The drawings are merely schematic representations, not intended to portray specific parameters of the invention. The drawings are intended to depict only typical embodiments of the invention. In the drawings, like numbering represents like elements.

DETAILED DESCRIPTION

Figure 1:
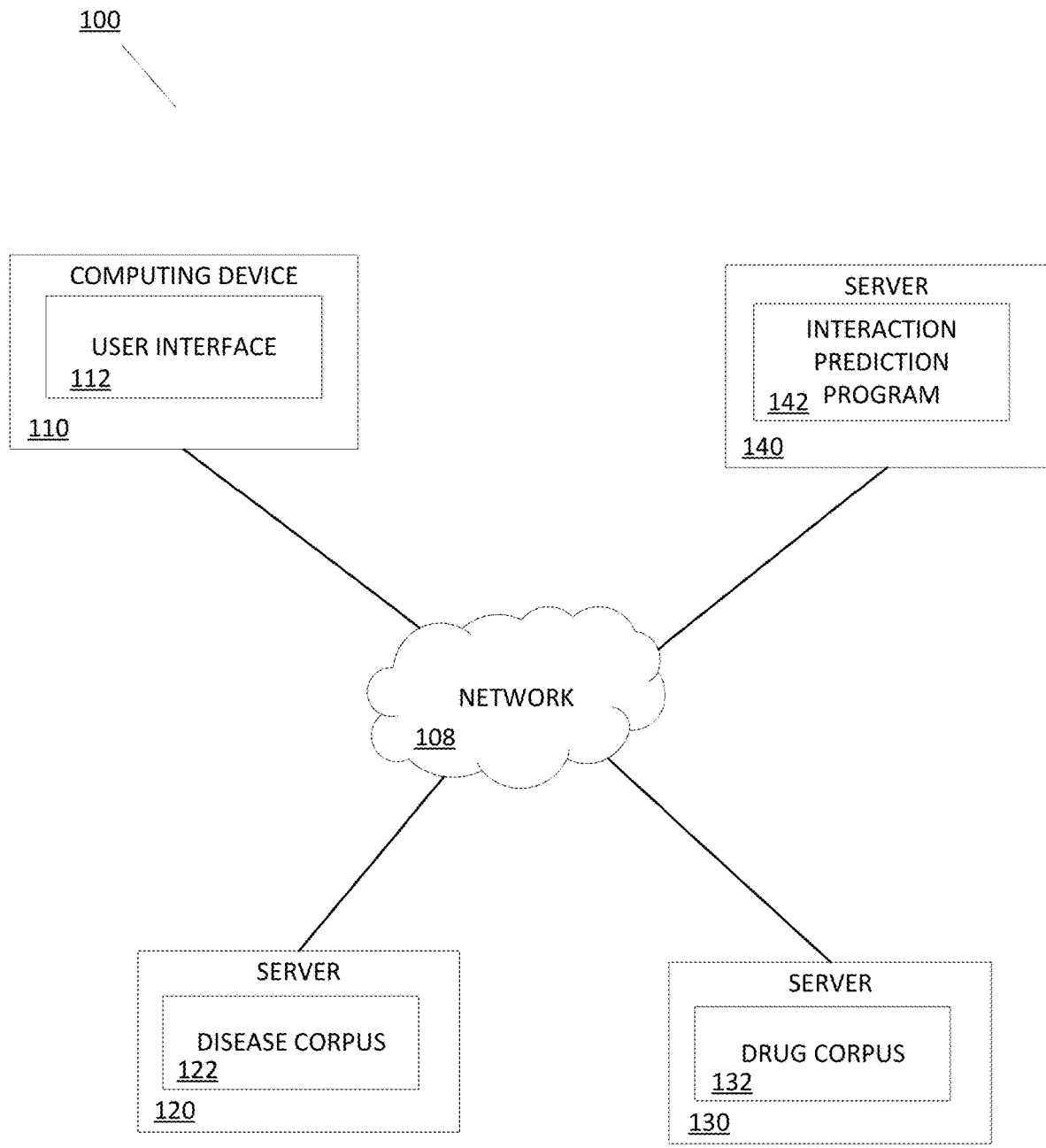
FIG. 1 depicts a schematic diagram of interaction prediction system 100, in accordance with an embodiment of the present invention.

Detailed embodiments of the claimed structures and methods are disclosed herein; however, it can be understood that the disclosed embodiments are merely illustrative of the claimed structures and methods that may be embodied in various forms. This invention may, however, be embodied in many different forms and should not be construed as limited to the exemplary embodiments set forth herein. Rather, these exemplary embodiments are provided so that this disclosure will be thorough and complete and will fully convey the scope of this invention to those skilled in the art. In the description, details of well-known features and techniques may be omitted to avoid unnecessarily obscuring the presented embodiments.

References in the specification to "one embodiment", "an embodiment", "an example embodiment", etc., indicate that the embodiment described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it is submitted that it is within the knowledge of one skilled in the art to implement such feature, structure, or characteristic in connection with other embodiments whether or not explicitly described.

In the interest of not obscuring the presentation of embodiments of the present invention, in the following detailed description, some processing steps or operations that are known in the art may have been combined together for presentation and for illustration purposes and in some instances may have not been described in detail. In other instances, some processing steps or operations that are known in the art may not be described at all. It should be understood that the following description is focused on the distinctive features or elements of various embodiments of the present invention.

The present invention performs several key functions, including assessing drug-disease interactions using drug-drug similarities, disease-disease similarities, and known drug-disease interactions from expert-curated knowledge bases and literature. In addition, and based at least in part on the assessments, the present invention predicts drug-disease interactions through large-scale similarity-based link prediction. Lastly, the invention generates an interaction score for candidate drug-disease pairs, which may be used for various functions, including decision support and as a factor in an integrated causality assessment.

Despite the advances made in drug development and safety, unanticipated drug-disease interactions are still a common occurrence in medical practice. This may be for several reasons, the first being that clinical trials often fail to reveal rare toxicity of certain drugs given the limited size and length of clinical studies. For example, a typical clinical trial for any drug is limited to very few patients, e.g., 1500, and only for rather a short period of time, e.g., 2-3 months. Utilizing a population and duration of such limited size is simply not an accurate enough representation of the true administration of a drug to ascertain all of its impacts once offered to millions of patients for a much longer period of time. Moreover, clinical trials often fail to test for interactions when drugs are taken in combination, and therefore unanticipated interactions occur more frequently for patients who are prescribed or otherwise consume a multi-drug regimen. In fact, it is well known that adverse reactions increase exponentially when taking four or more drugs simultaneously and, therefore, the rare toxicity of newly developed drugs (especially when taken in unanticipated combinations) cannot be established until after the drug becomes widely available in the market. Second, healthcare providers often fail to report adverse drug interactions and reactions because of the misconception that all severe adverse drug reactions are already known when a drug is brought to the market. The present invention intends to reduce or prevent adverse drug-disease interactions by predicting these interactions before they occur using large scale, similarity-based link prediction.

A interaction prediction system 100, in accordance with embodiments of the present invention, is illustrated by FIG. 1. In the example embodiment, interaction prediction system 100 includes computing device 110, server 120, server 130, and server 140, all interconnected via network 108. While, in the example embodiment, programming and data of the present invention are stored and accessed remotely across several servers via network 108, in other embodiments, programming and data of the present invention may be stored locally on as few as one physical computing device or amongst other computing devices than those depicted.

In the example embodiment, network 108 is a communication channel capable of transferring data between connected devices. In the example embodiment, network 108 is the Internet, representing a worldwide collection of networks and gateways to support communications between devices connected to the Internet. Moreover, network 108 may include, for example, wired, wireless, or fiber optic connections which may be implemented as an intranet network, a local area network (LAN), a wide area network (WAN), or a combination thereof. In further embodiments, network 108 may be a Bluetooth network, a WiFi network, or a combination thereof. In yet further embodiments, network 108 may be a telecommunications network used to facilitate telephone calls between two or more parties comprising a landline network, a wireless network, a closed network, a satellite network, or a combination thereof. In general, network 108 can be any combination of connections and protocols that will support communications between computing device 110, server 120, server 130, and server 140.

In the example embodiment, computing device 110 includes user interface 112 and may be a server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While computing device 110 is shown as a single device, in other embodiments, computing device 110 may be comprised of a cluster or plurality of computing devices, working together or working separately. Computing device 110 is described in greater detail with reference to FIG. 4.

User interface 112 is a software application which allows a user of computing device 110 to interact with computing device 110 and other connected devices via network 108. In addition, user interface 112 may be connectively coupled to hardware components, such as those depicted by FIG. 4, for receiving user input, including mice, keyboards, touchscreens, microphones, cameras, and the like. In the example embodiment, user interface 112 is implemented via a web browsing application that is capable of transferring data files, folders, audio, video, hyperlinks, compressed data, and other forms of data transfer individually or in bulk. In other embodiments, user interface 112 may be implemented via other integrated or standalone software applications and hardware capable of receiving user input and communicating with other electronic devices.

In the example embodiment, server 120 includes disease corpus 122 and may be a server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While server 120 is shown as a single device, in other embodiments, server 120 may be comprised of a cluster or plurality of computing devices, working together or working separately. Server 120 is described in greater detail with reference to FIG. 4.

Disease corpus 122 is a collection of data contained in files, folders, and other document types. In particular, and as used in the example embodiment, disease corpus 122 details numerous diseases, conditions, ailments, etc. For example, disease corpus 122 may be a database accessed via network 108 which stores drug data in XML, relational, non-relational, and CSV formats. Data contained in disease corpus 122 may include that detailed by a variety of sources, such as websites and databases corresponding to foundations, research institutions, universities, hospitals, medical facilities, clinicians, federal agencies, insurance companies, and other entities that maintain records detailing drugs, diseases, and health/healthcare information. Moreover, such data includes disease information and characteristics, such as conditions, side effects, severity, causes, duration, catalysts/ exacerbators, inhibitors, treatments/cures, treatment effectiveness, host measurements (red/white blood cells, hormone levels, temperature, etc.), and the like. In other embodiments, however, disease corpus 122 may detail other bodies of categorized and subject specific data, such as legal, financial, medical, etc. data, or include uncategorized data of miscellaneous topics. In the example embodiment, disease corpus 122 may be structured, partially structured, or unstructured. Moreover, data within disease corpus 122 may be written in programming languages of common file formats such as .docx, .doc, .pdf, .rtf, .jpg, .csv, .txt, etc. In further embodiments, disease corpus 122 may include handwritten and other documents scanned or otherwise converted into electronic form.

In the example embodiment, server 130 includes drug corpus 132 and may be a server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While server 130 is shown as a single device, in other embodiments, server 130 may be comprised of a cluster or plurality of computing devices, working together or working separately. Server 130 is described in greater detail with reference to FIG. 4.

Drug corpus 132 is a collection of data contained in files, folders, and other document types. In particular, and as used in the example embodiment, drug corpus 132 details drugs and medications. For example, drug corpus 132 may be a database accessed via network 108 which stores drug data in XML, relational, non-relational, and CSV formats. Data contained in drug corpus 132 may include that detailed by a variety of sources, such as websites and databases corresponding to foundations, research institutions, universities, hospitals, medical facilities, clinicians, federal agencies, insurance companies, and other entities that maintain records detailing drugs, diseases, and health/healthcare information. Moreover, such data includes active chemical ingredients, recommended dosage, restrictions, conflicts, and the like. In other embodiments, however, drug corpus 132 may detail other bodies of categorized and subject specific data, such as legal, financial, medical, etc. data, or include uncategorized data of miscellaneous topics. In the example embodiment, drug corpus 132 may be structured, partially structured, or unstructured. Moreover, data within drug corpus 132 may be written in programming languages of common file formats such as .docx, .doc, .pdf, .rtf, .jpg, .csv, .txt, etc. In further embodiments, drug corpus 132 may include handwritten and other documents scanned or otherwise converted into electronic form.

In the example embodiment, server 140 includes interaction prediction program 142 and may be a server, a laptop computer, a notebook, a tablet computer, a netbook computer, a personal computer (PC), a desktop computer, a server, a personal digital assistant (PDA), a rotary phone, a touchtone phone, a smart phone, a mobile phone, a virtual device, a thin client, or any other electronic device or computing system capable of receiving and sending data to and from other computing devices. While server 140 is shown as a single device, in other embodiments, server 140 may be comprised of a cluster or plurality of computing devices, working together or working separately. Server 140 is described in greater detail with reference to FIG. 4.

In the example embodiment, interaction prediction program 142 is a software application capable of ingesting drug and disease data to generate a knowledge graph and, based on the knowledge graph, construct one or more drug-drug similarity measures and one or more disease-disease similarity measures. In addition, interaction prediction program 142 is capable of identifying known drug-disease interactions and, based on the constructed similarities and identified known interactions, building adjusted logistic regression models describing the data. What's more, interaction prediction program 142 is capable of generating drug-disease pair feature vectors and building a model describing the effect of the similarity features on a likelihood of an interaction between candidate drug-disease pairs. Interaction prediction program 142 is further capable of applying the model to candidate drug-disease pairs in order to generate an interaction score, as well as determine whether the interaction score exceeds a threshold. If interaction prediction program 142 determines that the interaction score exceeds the threshold, interaction prediction program 142 is capable of modifying the patient drug regimen before recalculating an interaction score for comparison to the threshold. Alternatively, if interaction prediction program 142 determines that the interaction score does not exceed the threshold, interaction prediction program 142 ends.

Figure 2:
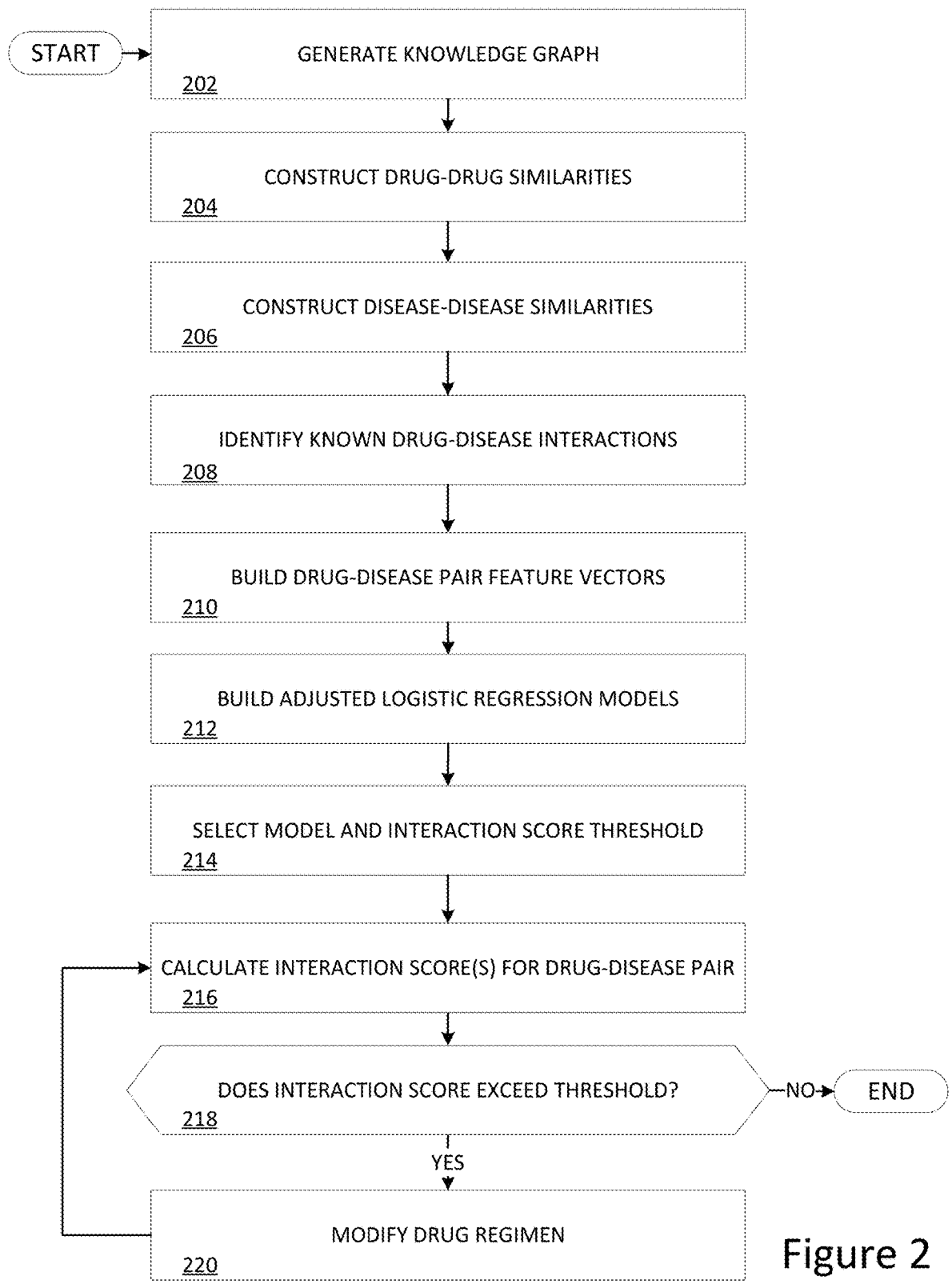
FIG. 2 depicts a flowchart illustrating the operations of interaction prediction program 142 of interaction prediction system 100 in identifying drug-disease interactions, in accordance with an embodiment of the present invention.

FIG. 2 illustrates the operations of interaction prediction program 142 of interaction prediction system 100 in predicting patient prescription drug and disease interactions.

Interaction prediction program 142 generates a knowledge graph (step 202). A knowledge graph describes entities and their interrelations through an organized graph. In the example embodiment, interaction prediction program 142 generates a knowledge graph by first ingesting expert-curated drug and disease data from drug corpus 132 and disease corpus 122, respectively, in various data formats, such as XML, relational, non-relational, and CSV formats. In embodiments, the expert curated data that interaction prediction program 142 ingests from drug corpus 132 and disease corpus 122 may, for example, include websites and databases corresponding to foundations, research institutions, universities, hospitals, medical facilities, clinicians, federal agencies, insurance companies, and other entities that maintain records detailing drugs, diseases, and health/healthcare information. Moreover, interaction prediction program 142 may reference data from sources within the public domain, or that made available under the Creative Common's Attribution-NonCommerical-ShareAlike 4.0 International License.

More particularly, and in the example embodiment, interaction prediction program 142 ingests information from drug corpus 132 that includes drug and disease data from DrugBank® (Drugbank® is a registered trademark of The Governors University of Alberta and OMx Personal Health Analytics, Inc.), gene interaction data from the Comparative Taxicogenomics Database® (CTD® is a registered trademark of the MDI Biological Laboratory and NC State University), gene function and structure data from Uniprot, genetic and protein interaction data from the BioGRID database, biomedical vocabularies data that include the NCBI taxonomy from the Unified Medical Language System, gene information from the Gene Ontology (GO), data from the MedicalSubject Headings (MeSH), and drug classification reference model data from the National Drug File-Reference Terminology (NDF-RT).

Similarly, and in the example embodiment, interaction prediction program 142 ingests information from disease corpus 122 that includes, for example, data from the DisGeNet Discovery Platform, the DisSim Web Application, and the Phenotype Associations Dataset. In other embodiments, interaction prediction program 142 may alternatively or additionally reference alternative corpora, and/or ingest drug and disease data uploaded via user interface 112 of computing device 110.

Figure 3:
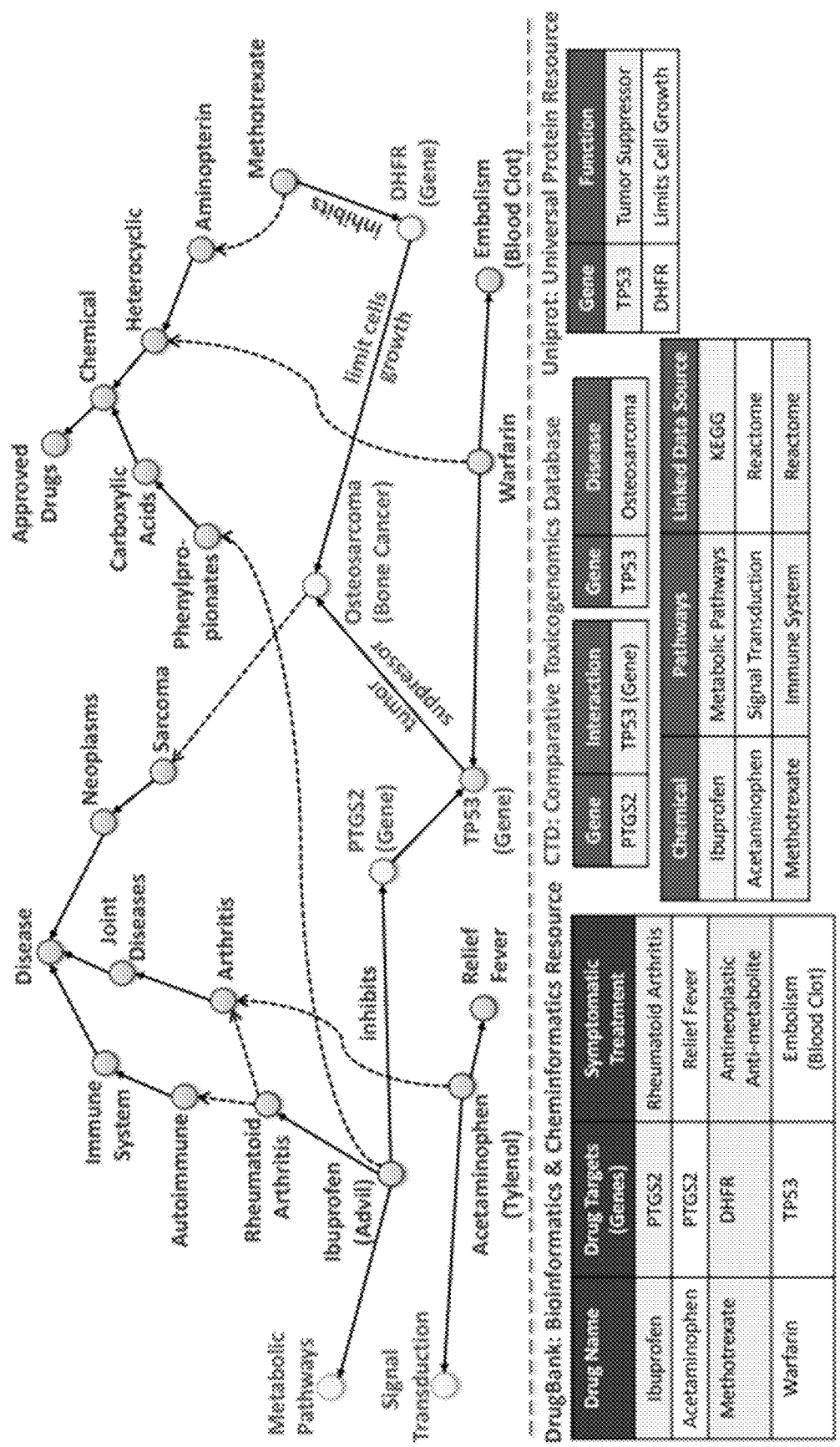
FIG. 3 depicts an example knowledge graph, in accordance with an embodiment of the present invention.

For example, and with reference to the tables illustrated by FIG. 3, interaction prediction program 142 references DrugBank® to ingest information relating to drugs, drug targets, and symptomatic treatment. Moreover, interaction prediction program 142 references the CTD® to ingest information relating to genes, interactions, diseases, chemicals, pathways, and linked data sources. Further, interaction prediction program 142 references Uniprot to ingest information relating to genes and functions.

Interaction prediction program 142 then generates a knowledge graph based on the ingested information (step 202 continued). In curating the knowledge graph, interaction prediction program 142 captures data interconnectedness by identifying entities, attributes, and relations, including relations to other entities and relations of the entity attributes to data values. Because the data may be ingested from a variety of sources, in various embodiments interaction prediction program 142 may be configured to connect the entities and relationships described by each of the sources, thereby creating a cohesive knowledge graph capable of being further enriched through additional data ingestion. Moreover, interaction prediction program 142 may be configured to re-evaluate existing entity connections, as many existing linkages are performed statically and may thus be outdated or even non-existent. In order to overcome other challenges associated with constructing a unified view of the data, interaction prediction program 142 employs entity resolution methodology through, for example, statistical disambiguation (e.g., cosine similarity, edit distance, or language model techniques) or through semantic analysis by examining the conceptual property of entities. These techniques are not only essential to identify similar entities, but also instrumental in designing and capturing similarities among entities in order to engineer features necessary to enable interaction predictions. Thus, using the above methods, interaction prediction program 142 constructs a knowledge graph linking the entities and relationships found within the ingested data.

For example, FIG. 3 depicts a knowledge graph having an identifier for the drug (i.e., entity) Methotrexate. As illustrated, the knowledge graph captures Methotrexate attributes, including its molecular structure and mechanism of actions. The graph also captures its relations to other entities, including genes that Methotrexate targets (i.e., DHFR), and, subsequently, conditions that it treats (Osteosarcoma) that are reachable through its target genes.

Interaction prediction program 142 constructs drug-drug similarity measures (step 204). In the example embodiment, interaction prediction program 142 constructs multi-dimensional drug profiles detailing drug attributes, such as chemical Structure, drug target, chemical-protein interactome (CPI) profiles, drug mechanism of action, anatomical therapeutic chemical (ATC), enzyme, medical subject headings (MeSH) category, side effect, and the like. In the example embodiment, interaction prediction program 142 assesses drug-drug similarity measures and disease-disease similarity measures to identify similarities to drug-disease pairs having known interactions, or known drug-disease interactions (KDDI). For each drug-disease pair, interaction prediction program 142 determines a drug similarity score based on a drug similarity function, sim, which, in the example embodiment, is normalized between 0-1 with a higher drug similarity score indicating a greater similarity between the two drug pairs. In the example embodiment, interaction prediction program 142 repeats this process for each pair of ingested drugs until all pairs have been assessed. The entire set of drug similarity measures, sim, is denoted by SIM. In the example embodiment, interaction prediction program 142 may construct drug similarity measures that may include, but are not limited to, the following dimensions:

Chemical-protein interactome (CPI) profile based similarity: The chemical-protein interactome (CPI) profile of a drug d, denoted cpi(d), is a vector indicating how well its chemical structure docks or binds with roughly 611 human Protein Data Bank (PDB) structures associated with drug-drug interactions. The CPI profile based similarity of two drugs d1 and d2 is computed as the cosine similarity between the mean-centered versions of vectors cpi(d1) and cpi(d2).

Mechanism of action based similarity: For a drug d, interaction prediction program 142 collects all its mechanisms of action obtained from NDF-RT. To discount popular terms, inverse document frequency (IDF) is used to assign more weight to relatively rare mechanism of actions: IDF(t, Drugs)=log |Drugs|+1 DF (t,Drugs)+1 where Drugs is the set of all drugs, t is a mechanism of action, and DF(t, Drugs) is the number of drugs with the mechanism of action t. The IDF-weighted mechanism of action vector of a drug d is a vector moa(d) whose components are mechanisms of action. The value of a component t of moa(d), denoted moa(d)[t], is zero if t is not a known mechanism of action of d; otherwise, it is IDF(t, Drugs). The mechanism of action based similarity measure of two drugs d1 and d2 is the cosine similarity of the vectors moa(d1) and moa(d2).

Physiological effect based similarity: For a drug d, interaction prediction program 142 collects all its physiological effects obtained from NDF-RT. The physiological effect based similarity measure of two drugs d1 and d2 is defined as the cosine similarity of IDF-weighted physiological effect vectors of the two drugs, which are computed in the same way as the IDF-weighted mechanism of action vector described above.

Pathways based similarity: Interaction prediction program 142 collects information about pathways affected by drugs from the CTD database. The pathways based similarity of two drugs is defined as the cosine similarity between the IDF-weighted pathways vectors of the two drugs, which are computed in a similar way as IDF-weighted mechanism of action vectors described above.

Side effect based similarity: Interaction prediction program 142 collects side effects associated with a drug from the Side Effect Resource (SIDER) database of drug side effects. The side effect based similarity of two drugs is defined as the cosine similarity between the IDF-weighted side effect vectors of the two drugs, which are computed in a similar way as IDF-weighted mechanism of action vectors of drugs described above.

Metabolizing enzyme based similarities: interaction prediction program 142 obtains information about enzymes responsible for the metabolism of drugs from DrugBank. Interaction prediction program 142 defines two drug similarity measures related to metabolizing enzymes. The first measure compares drugs based on the commonality of the metabolizing enzymes they interact with. However, it does not take into account the nature of the interaction (i.e., inhibitor, substrate, or inducer). It is formally defined as the cosine similarity between the IDF-weighted metabolizing enzyme vectors of two drugs, which are computed in a similar way as the IDF-weighted mechanism of action vectors of drugs described above. The second measure takes into account the nature of the interaction. For example, if drug d1 interacts with a single metabolizing enzyme e by acting as an inhibitor, while drug d2 also interacts only with the same enzyme e but as an inducer. According to the first measure, d1 and d2 will have a similarity value of 1. However, once the nature of the interaction with the enzyme is taken into account, it is clear that d1 and d2 are actually very dissimilar. Formally, to take into account the nature of the interaction, interaction prediction program 142 modifies the IDF-weighted metabolizing enzyme vector me(d) of a drug d by multiplying by −1 the value of each component corresponding to an enzyme that is inhibited by the drug. The similarity between two drugs is then defined as the normalized cosine similarity between the modified IDF-weighted metabolizing enzyme vectors of the two drugs (normalization ensures that the value remains in the [0, 1] range instead of [−1, 1] range).

Drug target based similarities: interaction prediction program 142 obtains information about proteins targeted by a drug from DrugBank. Here, interaction prediction program 142 defines three drug similarity measures related to drug targets. The first two are constructed in a similar way as the two metabolizing enzyme based similarities, in that the first similarity ignores the nature of the action of the drug on a protein target (i.e., inhibition or activation), whereas the second takes it into account. The third similarity measure compares drugs based on the molecular functions of their protein targets as defined in Uniprot using Gene Ontology (GO) annotations. More specifically, the third similarity measure is computed as Resnik semantic similarity.

Chemical structure similarity: interaction prediction program 142 obtains the chemical structures of drugs from DrugBank in the simplified molecular-input line-entry system (SMILES) format. Using the Chemical Development Kit (CDK), with default setting, the fingerprints of the molecular structures of drugs are computed as bit vectors. The chemical structure similarity of two drugs is then computed as the Jaccard similarity (or Tanimoto coefficient) of their fingerprints.

Anatomical therapeutic chemical (ATC) classification system based similarity: ATC is a classification of the active ingredients of drugs according to the organs that they affect as well as their chemical, pharmacological, and therapeutic characteristics. The classification consists of multiple trees representing different organs or systems affected by drugs, and different therapeutical and chemical properties of drugs. Interaction prediction program 142 obtains the ATC codes associated with each drug from DrugBank. For a given drug, interaction prediction program 142 collects all its ATC code from DrugBank to build a ATC code vector (the most specific ATC codes XI associated with the drug (i.e., leaves of the classification tree) and also all the ancestor codes are included). The ATC based similarity of two drugs is defined as the cosine similarity between the IDF-weighted ATC code vectors of the two drugs, which are computed in a similar way as IDF-weighted mechanism of action vectors described above.

MeSH based similarity: DrugBank associates each drug with a set of relevant MeSH (Medical Subject Heading) terms. The MeSH based similarity of two drugs is defined as the cosine similarity between the IDF-weighted MeSH vectors of the two drugs, which are computed in a similar way as IDF-weighted mechanism of action vectors of drugs described above.

In the example embodiment, the previously defined drug similarity measures rely on both cosine similarity and IDF (to discount popular terms). In other embodiments, however, other similarity metrics, such as weighted Jaccard or soft cosine similarity (when components of the vectors are elements of a taxonomical hierarchy, e.g., mechanism of action or physiological effect), and other means for discounting popular terms, such as entropy based weighting, may be implemented.

In the example embodiment, interaction prediction program 142 denotes the set of all drug similarity measures as SIM. Drug similarity measures in SIM need to be extended to produce drug-drug similarity measures that compare two pairs of drugs (e.g., a pair of candidate drugs against an already known interacting pair of drugs). SIM2 denotes the set of all drug-drug similarity measures derived from SIM. The power of similarity based approaches stems from not relying on a single similarity based prediction, but from combining all the individual independent predictions predict $[Sim_1 \otimes Sim_2, KDDI]$ for all $Sim_1 \otimes Sim_2 \in KDDI$ into a single score that indicates the level of confidence in the existence of a drug-drug interaction. In the example embodiment, interaction prediction program 142 combines all the individual predictions using arithmetic techniques, for example harmonic or geometric mean and, given a drug pair $(d_1, d_2)$, its feature vector consists of predict$[Sim_1 \otimes Sim_2, KDDI](d_1, d_2)$ for all $Sim_1 \otimes Sim_2 \in KDDI$.

For example, interaction prediction program 142 constructs drug-drug similarity scores in accordance with Table 1, below:

TABLE 1

| Drug - Drug Similarities | | |
|---|---|---|
| Drug1 | Drug2 | Similarity Score |
| Salsalate | Aspirin | 0.9 |
| Minoxidil | Felodipine | 0.7 |
| Salsalate | Aspirin | 0.7 |
| Minoxidil | Felodipine | 0.6 |
| . . . | . . . | . . . |
| Drug1i | Drug2i | simi |

Interaction prediction program 142 constructs disease-disease similarity measures (step 206). In the example embodiment, interaction prediction program 142 constructs multi-dimensional disease profiles detailing information regarding a disease ontology (DO), disease gene, disease phenotype, disease symptoms, disease comorbidity, disease pathology/morphology, etc. Interaction prediction program 142 then assesses diseases in pairs to determine similarities between each disease based on the above dimensions. For each pair of diseases, interaction prediction program 142 determines a disease similarity score which, in the example embodiment, is normalized between 0-1 with a higher disease similarity score indicating a greater similarity. In the example embodiment, interaction prediction program 142 repeats this process for each pair of ingested diseases until all pairs have been assessed. In addition, interaction prediction program 142 may be configured to periodically reassess disease similarity scores to ensure the assessment is relevant, for example recalculating the disease similarity scores at a prescribed frequency or detection of changes to data on which the assessment is made, e.g., writes to disease corpus 122.

In the example embodiment, disease-disease similarity measures may be based on semantics, ontology structure, DO, and/or leveraging information content. More particularly, for example, such similarity features may include application independent similarity measures, domain specific similarity measures, gene based similarity measures, process based similarity measures, phenotype based similarity measures, comorbidity based similarity measures, molecular/cellular based similarity measures, and/or multi-dimensional similarity measures. In the example embodiment, the disease-disease similarity measures may include any measures within the following, unexhaustive list:

Disease similarity of phenotypes, $S^{pheno}$: Disease phenotypes indicate phenotypic abnormalities encountered in human diseases. Interaction prediction program 142 constructs the phenotypic similarity by identifying similarity between the MeSH terms appearing in the medical description ("full text" and "clinical synopsis" fields) of diseases from Online Mendelian Inheritance in Man (OMIM) database. More specifically, interaction prediction program 142 represents each disease s in the OMIM by a K-dimensional (K is the number of the MeSH terms) MeSH term feature vector m(s), wherein each entry in the feature vector represents a MeSH term and the counts of the term found for disease s are the corresponding feature value. Interaction prediction program 142 then determines the pairwise disease phenotype similarity between two diseases s and s' as the cosine of the angle between their feature vectors, as shown by Equation 1:

$$S_{ss'}^{pheno} = \frac{\sum_{i=1}^{K} m(s)_i m(s')_i}{\sqrt{\sum_{i=1}^{K} m^2(s)_i} \sqrt{\sum_{i=1}^{K} m^2(s')_i}} \quad \text{Equation 1}$$

where $m(s)_i$ denotes the i-th entry of the feature vector m(s).

Disease similarity of disease ontology, $S^{do}$: The disease ontology (DO) is an open source ontological description of human disease, organized from a clinical perspective of disease etiology and location. In order to identify disease-disease similarities, interaction prediction program 142 first organizes terms for disease names and disease-related concepts within DO in a directed acyclic graph (DAG). In the example embodiment, the two linked diseases in DO are in an "is-a" relationship, which means one disease is a subtype of the other linked disease. The lower a disease is in DO hierarchy, the more specific the disease term is. In the example embodiment, interaction prediction program 142 calculates a semantic similarity between any pair of diseases by applying semantic similarity measures to the organized terms, in some embodiments using tools such as DOSim. For a disease term s in DO, the probability that the term is used in disease annotations is estimated as $p_s$, which is the number of disease term s or its descendants in DO, divided by the total number of disease terms in DO. Interaction prediction program 142 then defines a semantic similarity of two diseases s and s' as the information content of their lowest common ancestor in accordance with Equation 2, below:

$$S_{ss'}^{do} = -\log \min_{x \in C(s,s')} p_x \quad \text{Equation 2}$$

where C(s,s') is the set of all common ancestors of diseases s and s'.

Disease similarity of disease genes, $S^{gene}$: Disease-causing aberrations in the normal function of a gene define that gene as a disease gene. In order to identify disease similarities, interaction prediction program 142 collects all disease genes for each disease from "phenotype-gene relationships" field from OMIM database. Interaction prediction program 142 then calculates the pairwise disease similarity between diseases s and s' based on the average of sequence similarities of their disease gene sets in accordance with Equation 3:

$$S_{ss'}^{gene} = \frac{1}{|G(s)||G(s')|} \sum_{i=1}^{|G(s)|} \sum_{j=1}^{|G(s')|} SW(G_i(s), G_j(s')) \quad \text{Equation 3}$$

where for a given disease s and disease gene set G(s), |G(s)| is the size of the disease gene set of disease s. Interaction prediction program 142 then calculates a sequence similarity function of two disease genes as a Smith-Waterman sequence alignment score, SW.

Continuing the earlier introduced example, interaction prediction program 142 constructs disease-disease similarity measures in accordance with Table 2, below:

TABLE 2

Disease - Disease Similarities

| Disease1 | Disease2 | Similarity Score |
|---|---|---|
| Hypertension | Heart Failure | 0.6 |
| Asthma | COPD | 0.7 |
| Hypertension | Heart Failure | 0.5 |
| Asthma | COPD | 0.8 |
| ... | ... | ... |
| Disease1i | Disease2i | simi |

Interaction prediction program 142 identifies known drug-disease interactions (step 208). In the example embodiment, interaction prediction program 142 identifies known drug-disease interactions based on expert-curated knowledge bases and literature.

With reference again to an example, interaction prediction program 142 ingests known drug-disease interactions from DrugBank in accordance with Table 3, below:

TABLE 3

Known Drug - Disease Interactions

| Drug | Disease | Interaction |
|---|---|---|
| Minoxidil | Heart Failure | Yes |
| Metformin | Heart Failure | Yes |
| Nicotine | Hypertension | Yes |
| Aspirin | Asthma | Yes |

Interaction prediction program 142 builds drug-disease pair feature vectors (step 210). In the example embodiment, such feature vectors are used in comparing drug-disease pairs and are based on similarity features that include a max, mean over positive pairs, standard deviation over positive pairs, max Z value, mean over all pairs, and other statistical measures. As used herein, the Z value is defined by Equation 4, as:

$$z = \frac{x - \mu}{\sigma} \quad \text{Equation 4}$$

where μ is the mean of the data and σ is the standard deviation of the data. The absolute value of Z represents the distance between the raw score and the data mean in units of the standard deviation. In the example embodiment, the total number of similarity features is defined by multiplying a number of drug similarities determined in step 204 by a number of disease similarities determined in step 206 by a number of pair similarity features identified in step 210.

With reference to the example introduced above, interaction prediction program 142 builds drug-disease candidate pair feature vectors in accordance with Table 4, below:

TABLE 4

Candidate Features

| Drug | Disease | Feature Vector |
|---|---|---|
| Aspirin | COPD | [0.9, . . . , 0.7] |
| Minoxidil | Hypertension | [0.7, . . . , 0.4] |

Interaction prediction program 142 builds adjusted logistic regression models (step 212). In machine learning, algorithms are formed into mathematical models used to learn from and make predictions on data. In typical practice, building the model requires three datasets having a same probability distribution, known as a training dataset, a validation dataset, and a test dataset. The training dataset is used to train candidate algorithms, while the validation dataset is used to compare the performance of the algorithms and decide which one utilize. Lastly, the test dataset is used to obtain the performance characteristics of the chosen algorithm, including an accuracy, sensitivity, specificity, F-measure, and so on. In the example embodiment, interaction prediction program 142 constructs models which implement logistic regression, however other models may be implemented in other embodiments. In statistics, regression analysis is a set of statistical processes for estimating the relationships among variables, with particular usefulness for analysing data having several variables deterministic of a dependent variable. Such analyses focus on determining how each of the one or more independent variables affect the outcome of the dependent variable, which is often measured with a dichotomous variable in which there are only two possible outcomes. In the example embodiment, such logistic regression techniques are captured in adjusted models that process the drug and disease similarity features above, while using the known drug-disease interactions as training labels, to output interaction scores indicating a likelihood of a drug-disease pair interacting.

Thus, in the example embodiment, interaction prediction program 142 constructs a model using at least one training subset of the known drug-disease interactions as training data and the drug/disease similarity features identified above as variables. By indicating which known drug-disease pairs result in an outcome having an interaction and those that do not (e.g., [0,1] using a dichotomous variable), interaction prediction program 142 trains a model that describes the effect of each variable (e.g., through weighting) on a likelihood of an interaction between any drug-disease pair.

Continuing the earlier introduced example, interaction prediction program 142 builds adjusted logistic regression models describing the effect drug and disease features have on a likelihood of a drug-disease pair having an interaction.

Interaction prediction program 142 selects a model and interaction score threshold (step 214). In the example embodiment, interaction prediction program 142 constructs several logistic regression models describing the effect of the variables (i.e., drug and disease similarity features) on the output (i.e., presence of an interaction) and tests each model using a validation subset of the known drug-disease interaction data. In the example embodiment, interaction prediction program 142 may use various model fitting techniques to select a model which best fits the validation dataset, including methods such as the rule of ten, maximum likelihood estimation, iteratively reweighted least squares, and the like. Having selected a most accurate model based on the validation dataset, interaction prediction program 142 may then ascertain performance characteristics of the model my applying it to a test dataset and record characteristics such as accuracy, sensitivity, specificity, etc. In addition, interaction prediction program 142 identifies an appropriate threshold for use with the model. In the example embodiment, the threshold is determined via a parameter tuning step during cross-validation experiments. As used herein, the interaction threshold denotes the interaction score beyond which an interaction is likely.

With reference to the earlier-introduce example, interaction prediction program 142 selects a model having a best fit to the validation data which has an interaction score threshold of 0.8.

Interaction prediction program 142 calculates interaction score(s) for each drug-disease pair (step 216). In the example embodiment, interaction prediction program 142 calculates a single interaction score for each drug-disease pair using the model selected above. Specifically, interaction prediction program 142 applies the weights specified by the model to each of the drug and disease similarity features of the drug disease pair and computes an overall interaction score.

With reference to the earlier introduced example, interaction prediction program 142 applies the selected model to the drug-disease candidate pairs to compute interaction scores in accordance with Table 5, below:

TABLE 5

Drug - Disease Interaction Prediction

| Drug | Disease | Interaction Score |
|---|---|---|
| Ibuprofen | Asthma | 0.78 |
| Nisoldipine | Heart Failure | 0.94 |

Interaction prediction program 142 determines whether the determined interaction score exceeds the interaction score threshold (decision 218). In the example embodiment, interaction prediction program 142 considers interaction scores in excess of the interaction score threshold an indication that the drug-disease candidate pair are likely to have an interaction, while those interaction scores that are less than that of the interaction score threshold are not likely to have an interaction. In the example embodiment, the interaction score threshold is determined via parameter tuning of the model during validation, however in other embodiments may be determined alternatively or received via user input.

Continuing the example above, for instance, the drug-disease candidate pair Ibuprofen and Asthma are not likely to interact because the associated interaction score of 0.78 does not exceed the interaction score threshold of 0.8. Conversely, the drug-disease candidate pair Nisoldipine and heart failure are likely to have an interaction because the associated interaction score of 0.94 exceeds the interaction score threshold of 0.8.

If interaction prediction program 142 determines that the interaction score exceeds the interaction score threshold (decision 218 "YES" branch), interaction prediction program 142 modifies a drug regiment (step 220). In order to identify alternative drugs, interaction prediction program 142 searches the drug profiles stored in drug corpus 132 for a drug having a same therapeutic effect with less of or lacking the active chemical, ingredient, drug target, etc. that resulted in the excessive interaction score. As used herein, a same therapeutic effect may be any other drug that is intended for and/or treats a same or similar disease. In some embodiments, interaction prediction program 142 may be configured to reference previous regimens of the patient and/or similar patients to determine an alternative drug that is most effective at mitigating the interaction score, yet sufficiently administer the desired therapeutic effect.

In addition, or alternatively, interaction prediction program 142 may take further action when predicting a drug-disease interaction. To that point, interaction prediction program 142 may make recommendations as to how the interaction, or side effect, can be better managed by the patient. In one embodiment, interaction prediction program 142 may identify the likely interaction based on the analysis above and suggest means for mitigating the interaction. For example, if interaction prediction program 142 predicts that an interaction will cause nausea, then interaction prediction program 142 may suggest purchasing an over the counter nausea medicine. In another example, if interaction prediction program 142 determines that an interaction will cause drowsiness, interaction prediction program 142 may suggest taking the drugs at night before bed. In further embodiments, interaction prediction program 142 may be further configured to utilize the interaction scores in a causality assessment.

With reference to the example above where the interaction score for the drug-disease candidate pair Nisoldipine and heart failure exceeds the interaction score threshold, interaction prediction program 142 identifies antihypertensive agents (e.g., diuretics and ACE inhibitors) other than calcium channel blockers as a replacement for Nisoldipine. Alternatively, interaction prediction program 142 may suggest avoiding particular activities immediately after taking Nisoldipine.

Interaction prediction program 142 recalculates the interaction score(s) for the modified drug regimen (step 216). In the example embodiment, interaction prediction program 142 recalculates the interaction score(s) in much the same manner as above, however in this case interaction prediction program 142 calculates interaction score(s) in consideration of the modifications made to the drug regimen. Interaction prediction program 142 then determines again whether the determined interaction score exceeds the interaction score threshold in much the same manner as that described above.

With reference again to the example above, interaction prediction program 142 determines an interaction score of 0.69 for the drug-disease pair candidates bumetanide and heart failure, thereby falling below the interaction score threshold.

Based on determining that the interaction score does not exceed the interaction score threshold (decision 218 "NO" branch), interaction prediction program 142 ends.

Figure 4:
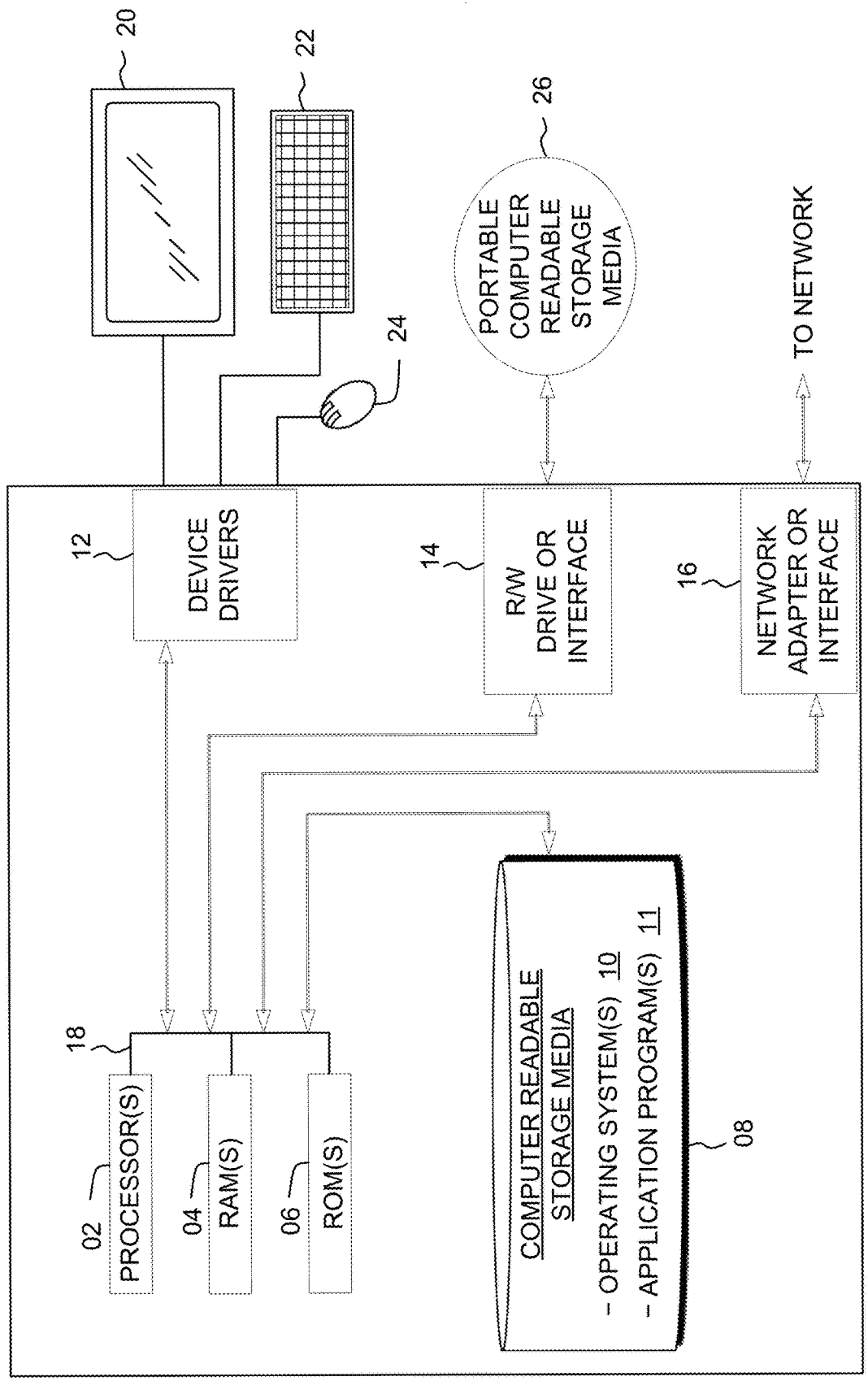
FIG. 4 depicts a block diagram depicting the hardware components of interaction prediction system 100 of FIG. 1, in accordance with an embodiment of the present invention.

FIG. 4 depicts a block diagram of computing device 110, server 120, server 130, and server 140 of interaction prediction system 100 of FIG. 1, in accordance with an embodiment of the present invention. It should be appreciated that FIG. 4 provides only an illustration of one implementation and does not imply any limitations with regard to the environments in which different embodiments may be implemented. Many modifications to the depicted environment may be made.

Computing device 110 may include one or more processors 02, one or more computer-readable RAMs 04, one or more computer-readable ROMs 06, one or more computer readable storage media 08, device drivers 12, read/write drive or interface 14, network adapter or interface 16, all interconnected over a communications fabric 18. Communications fabric 18 may be implemented with any architecture designed for passing data and/or control information between processors (such as microprocessors, communications and network processors, etc.), system memory, peripheral devices, and any other hardware components within a system.

One or more operating systems 10, and one or more application programs 11, for example interaction prediction program 142, are stored on one or more of the computer readable storage media 08 for execution by one or more of the processors 02 via one or more of the respective RAMs 04 (which typically include cache memory). In the illustrated embodiment, each of the computer readable storage media 08 may be a magnetic disk storage device of an internal hard drive, CD-ROM, DVD, memory stick, magnetic tape, magnetic disk, optical disk, a semiconductor storage device such as RAM, ROM, EPROM, flash memory or any other computer-readable tangible storage device that can store a computer program and digital information.

Computing device 110 may also include a R/W drive or interface 14 to read from and write to one or more portable computer readable storage media 26. Application programs 11 on said devices may be stored on one or more of the portable computer readable storage media 26, read via the respective R/W drive or interface 14 and loaded into the respective computer readable storage media 08.

Computing device 110 may also include a network adapter or interface 16, such as a TCP/IP adapter card or wireless communication adapter (such as a 4G wireless communication adapter using OFDMA technology). Application programs 11 on said computing devices may be downloaded to the computing device from an external computer or external storage device via a network (for example, the Internet, a local area network or other wide area network or wireless network) and network adapter or interface 16. From the network adapter or interface 16, the programs may be loaded onto computer readable storage media 08. The network may comprise copper wires, optical fibers, wireless transmission, routers, firewalls, switches, gateway computers and/or edge servers.

Computing device 110 may also include a display screen 20, a keyboard or keypad 22, and a computer mouse or touchpad 24. Device drivers 12 interface to display screen 20 for imaging, to keyboard or keypad 22, to computer mouse or touchpad 24, and/or to display screen 20 for pressure sensing of alphanumeric character entry and user selections. The device drivers 12, R/W drive or interface 14 and network adapter or interface 16 may comprise hardware and software (stored on computer readable storage media 08 and/or ROM 06).

The programs described herein are identified based upon the application for which they are implemented in a specific embodiment of the invention. However, it should be appreciated that any particular program nomenclature herein is used merely for convenience, and thus the invention should not be limited to use solely in any specific application identified and/or implied by such nomenclature.

Based on the foregoing, a computer system, method, and computer program product have been disclosed. However, numerous modifications and substitutions can be made without deviating from the scope of the present invention.

Therefore, the present invention has been disclosed by way of example and not limitation.

It is to be understood that although this disclosure includes a detailed description on cloud computing, implementation of the teachings recited herein are not limited to a cloud computing environment. Rather, embodiments of the present invention are capable of being implemented in conjunction with any other type of computing environment now known or later developed.

Cloud computing is a model of service delivery for enabling convenient, on-demand network access to a shared pool of configurable computing resources (e.g., networks, network bandwidth, servers, processing, memory, storage, applications, virtual machines, and services) that can be rapidly provisioned and released with minimal management effort or interaction with a provider of the service. This cloud model may include at least five characteristics, at least three service models, and at least four deployment models.

Characteristics are as Follows:

On-demand self-service: a cloud consumer can unilaterally provision computing capabilities, such as server time and network storage, as needed automatically without requiring human interaction with the service's provider.

Broad network access: capabilities are available over a network and accessed through standard mechanisms that promote use by heterogeneous thin or thick client platforms (e.g., mobile phones, laptops, and PDAs).

Resource pooling: the provider's computing resources are pooled to serve multiple consumers using a multi-tenant model, with different physical and virtual resources dynamically assigned and reassigned according to demand. There is a sense of location independence in that the consumer generally has no control or knowledge over the exact location of the provided resources but may be able to specify location at a higher level of abstraction (e.g., country, state, or datacenter).

Rapid elasticity: capabilities can be rapidly and elastically provisioned, in some cases automatically, to quickly scale out and rapidly released to quickly scale in. To the consumer, the capabilities available for provisioning often appear to be unlimited and can be purchased in any quantity at any time.

Measured service: cloud systems automatically control and optimize resource use by leveraging a metering capability at some level of abstraction appropriate to the type of service (e.g., storage, processing, bandwidth, and active user accounts). Resource usage can be monitored, controlled, and reported, providing transparency for both the provider and consumer of the utilized service.

Service Models are as Follows:

Software as a Service (SaaS): the capability provided to the consumer is to use the provider's applications running on a cloud infrastructure. The applications are accessible from various client devices through a thin client interface such as a web browser (e.g., web-based e-mail). The consumer does not manage or control the underlying cloud infrastructure including network, servers, operating systems, storage, or even individual application capabilities, with the possible exception of limited user-specific application configuration settings.

Platform as a Service (PaaS): the capability provided to the consumer is to deploy onto the cloud infrastructure consumer-created or acquired applications created using programming languages and tools supported by the provider. The consumer does not manage or control the underlying cloud infrastructure including networks, servers, operating systems, or storage, but has control over the deployed applications and possibly application hosting environment configurations.

Infrastructure as a Service (IaaS): the capability provided to the consumer is to provision processing, storage, networks, and other fundamental computing resources where the consumer is able to deploy and run arbitrary software, which can include operating systems and applications. The consumer does not manage or control the underlying cloud infrastructure but has control over operating systems, storage, deployed applications, and possibly limited control of select networking components (e.g., host firewalls).

Deployment Models are as Follows:

Private cloud: the cloud infrastructure is operated solely for an organization. It may be managed by the organization or a third party and may exist on-premises or off-premises.

Community cloud: the cloud infrastructure is shared by several organizations and supports a specific community that has shared concerns (e.g., mission, security requirements, policy, and compliance considerations). It may be managed by the organizations or a third party and may exist on-premises or off-premises.

Public cloud: the cloud infrastructure is made available to the general public or a large industry group and is owned by an organization selling cloud services.

Hybrid cloud: the cloud infrastructure is a composition of two or more clouds (private, community, or public) that remain unique entities but are bound together by standardized or proprietary technology that enables data and application portability (e.g., cloud bursting for load-balancing between clouds).

A cloud computing environment is service oriented with a focus on statelessness, low coupling, modularity, and semantic interoperability. At the heart of cloud computing is an infrastructure that includes a network of interconnected nodes.

Figure 5:
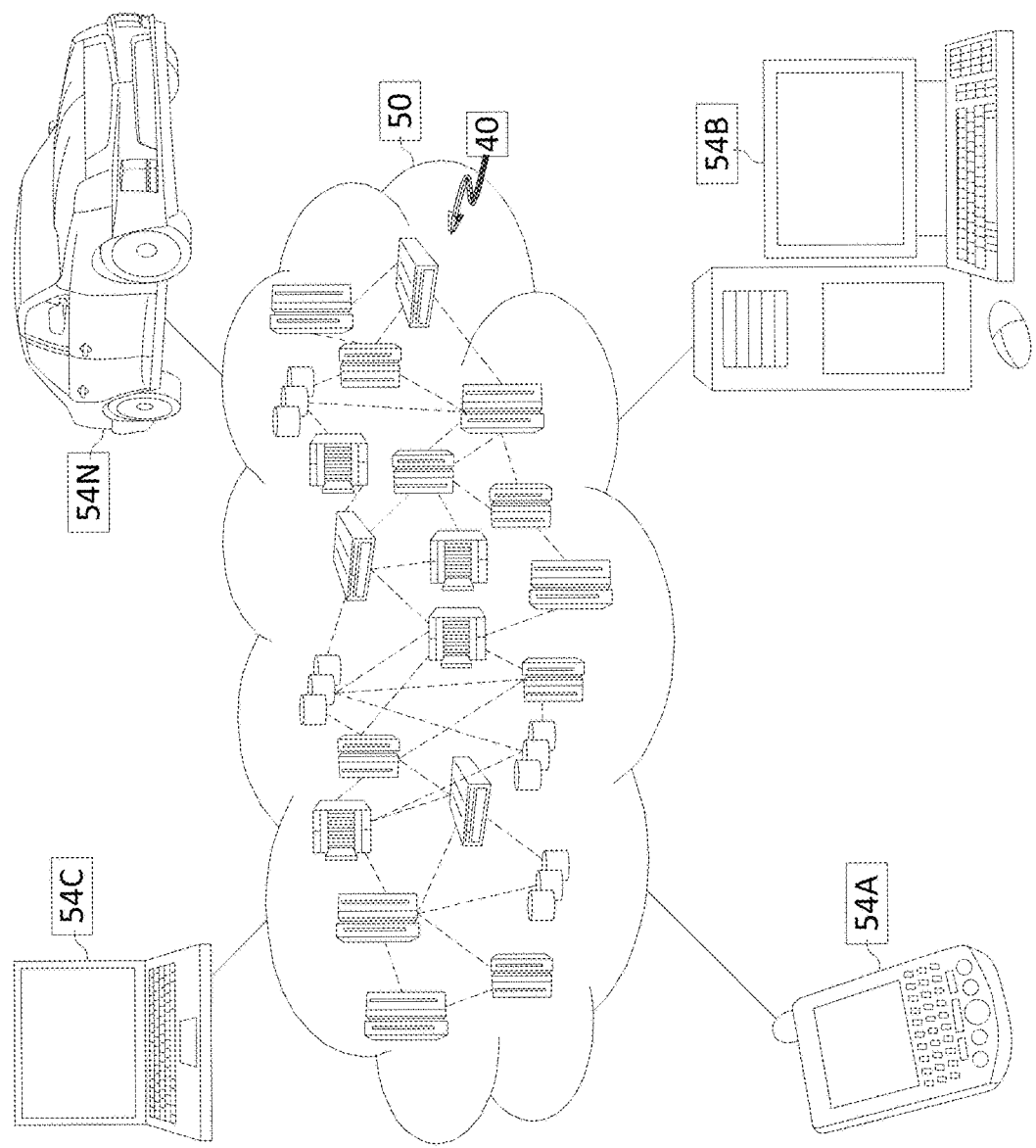
FIG. 5 depicts a cloud computing environment, in accordance with an embodiment of the present invention.
Figure 6:
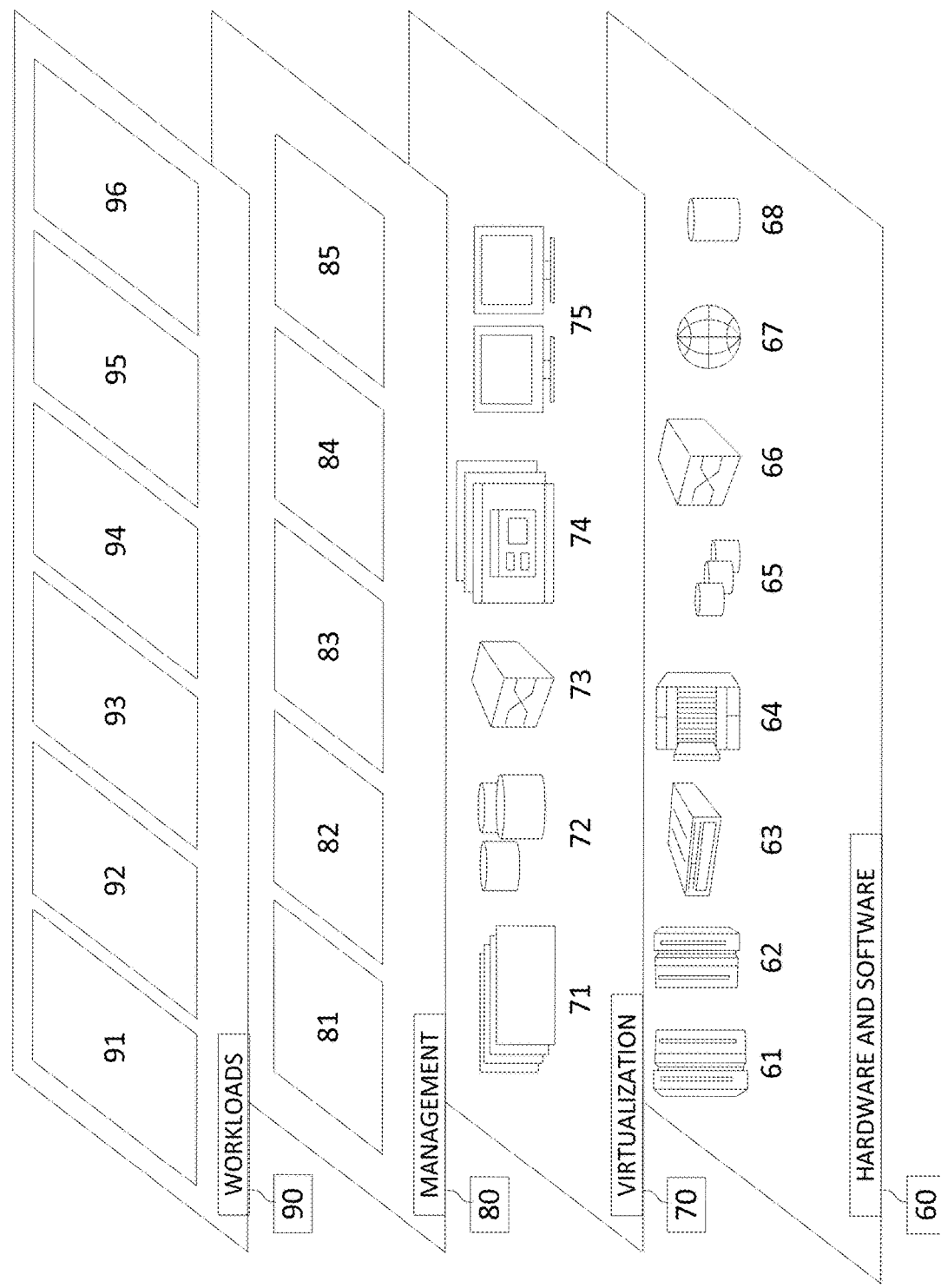
FIG. 6 depicts abstraction model layers, in accordance with an embodiment of the present invention.

Referring now to FIG. 5, illustrative cloud computing environment 50 is depicted. As shown, cloud computing environment 50 includes one or more cloud computing nodes 40 with which local computing devices used by cloud consumers, such as, for example, personal digital assistant (PDA) or cellular telephone 54A, desktop computer 54B, laptop computer 54C, and/or automobile computer system 54N may communicate. Nodes 40 may communicate with one another. They may be grouped (not shown) physically or virtually, in one or more networks, such as Private, Community, Public, or Hybrid clouds as described hereinabove, or a combination thereof. This allows cloud computing environment 50 to offer infrastructure, platforms and/or software as services for which a cloud consumer does not need to maintain resources on a local computing device. It is understood that the types of computing devices 54A-N shown in FIG. 4 are intended to be illustrative only and that computing nodes 40 and cloud computing environment 50 can communicate with any type of computerized device over any type of network and/or network addressable connection (e.g., using a web browser).

Referring now to FIG. 5, a set of functional abstraction layers provided by cloud computing environment 50 (FIG. 4) is shown. It should be understood in advance that the components, layers, and functions shown in FIG. 5 are intended to be illustrative only and embodiments of the invention are not limited thereto. As depicted, the following layers and corresponding functions are provided:

Hardware and software layer 60 includes hardware and software components. Examples of hardware components include: mainframes 61; RISC (Reduced Instruction Set Computer) architecture based servers 62; servers 63; blade servers 64; storage devices 65; and networks and networking components 66. In some embodiments, software components include network application server software 67 and database software 68.

Virtualization layer 70 provides an abstraction layer from which the following examples of virtual entities may be provided: virtual servers 71; virtual storage 72; virtual networks 73, including virtual private networks; virtual applications and operating systems 74; and virtual clients 75.

In one example, management layer 80 may provide the functions described below. Resource provisioning 81 provides dynamic procurement of computing resources and other resources that are utilized to perform tasks within the cloud computing environment. Metering and Pricing 82 provide cost tracking as resources are utilized within the cloud computing environment, and billing or invoicing for consumption of these resources. In one example, these resources may include application software licenses. Security provides identity verification for cloud consumers and tasks, as well as protection for data and other resources. User portal 83 provides access to the cloud computing environment for consumers and system administrators. Service level management 84 provides cloud computing resource allocation and management such that required service levels are met. Service Level Agreement (SLA) planning and fulfillment 85 provide pre-arrangement for, and procurement of, cloud computing resources for which a future requirement is anticipated in accordance with an SLA.

Workloads layer 90 provides examples of functionality for which the cloud computing environment may be utilized. Examples of workloads and functions which may be provided from this layer include: mapping and navigation 91; software development and lifecycle management 92; virtual classroom education delivery 93; data analytics processing 94; transaction processing 95; and drug decision support processing 96.

The present invention may be a system, a method, and/or a computer program product at any possible technical detail level of integration. The computer program product may include a computer readable storage medium (or media) having computer readable program instructions thereon for causing a processor to carry out aspects of the present invention.

The computer readable storage medium can be a tangible device that can retain and store instructions for use by an instruction execution device. The computer readable storage medium may be, for example, but is not limited to, an electronic storage device, a magnetic storage device, an optical storage device, an electromagnetic storage device, a semiconductor storage device, or any suitable combination of the foregoing. A non-exhaustive list of more specific examples of the computer readable storage medium includes the following: a portable computer diskette, a hard disk, a random access memory (RAM), a read-only memory (ROM), an erasable programmable read-only memory (EPROM or Flash memory), a static random access memory (SRAM), a portable compact disc read-only memory (CD-ROM), a digital versatile disk (DVD), a memory stick, a floppy disk, a mechanically encoded device such as punch-cards or raised structures in a groove having instructions recorded thereon, and any suitable combination of the foregoing. A computer readable storage medium, as used herein, is not to be construed as being transitory signals per se, such as radio waves or other freely propagating electromagnetic waves, electromagnetic waves propagating through a waveguide or other transmission media (e.g., light pulses passing through a fiber-optic cable), or electrical signals transmitted through a wire.

Computer readable program instructions described herein can be downloaded to respective computing/processing devices from a computer readable storage medium or to an external computer or external storage device via a network, for example, the Internet, a local area network, a wide area network and/or a wireless network. The network may comprise copper transmission cables, optical transmission fibers, wireless transmission, routers, firewalls, switches, gateway computers and/or edge servers. A network adapter card or network interface in each computing/processing device receives computer readable program instructions from the network and forwards the computer readable program instructions for storage in a computer readable storage medium within the respective computing/processing device.

Computer readable program instructions for carrying out operations of the present invention may be assembler instructions, instruction-set-architecture (ISA) instructions, machine instructions, machine dependent instructions, microcode, firmware instructions, state-setting data, configuration data for integrated circuitry, or either source code or object code written in any combination of one or more programming languages, including an object oriented programming language such as Smalltalk, C++, or the like, and procedural programming languages, such as the "C" programming language or similar programming languages. The computer readable program instructions may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider). In some embodiments, electronic circuitry including, for example, programmable logic circuitry, field-programmable gate arrays (FPGA), or programmable logic arrays (PLA) may execute the computer readable program instructions by utilizing state information of the computer readable program instructions to personalize the electronic circuitry, in order to perform aspects of the present invention.

Aspects of the present invention are described herein with reference to flowchart illustrations and/or block diagrams of methods, apparatus (systems), and computer program products according to embodiments of the invention. It will be understood that each block of the flowchart illustrations and/or block diagrams, and combinations of blocks in the flowchart illustrations and/or block diagrams, can be implemented by computer readable program instructions.

These computer readable program instructions may be provided to a processor of a general purpose computer, special purpose computer, or other programmable data processing apparatus to produce a machine, such that the instructions, which execute via the processor of the computer or other programmable data processing apparatus, create means for implementing the functions/acts specified in the flowchart and/or block diagram block or blocks. These computer readable program instructions may also be stored in a computer readable storage medium that can direct a computer, a programmable data processing apparatus, and/or other devices to function in a particular manner, such that the computer readable storage medium having instructions stored therein comprises an article of manufacture including instructions which implement aspects of the function/act specified in the flowchart and/or block diagram block or blocks.

The computer readable program instructions may also be loaded onto a computer, other programmable data processing apparatus, or other device to cause a series of operational steps to be performed on the computer, other programmable apparatus or other device to produce a computer implemented process, such that the instructions which execute on the computer, other programmable apparatus, or other device implement the functions/acts specified in the flowchart and/or block diagram block or blocks.

The flowchart and block diagrams in the Figures illustrate the architecture, functionality, and operation of possible implementations of systems, methods, and computer program products according to various embodiments of the present invention. In this regard, each block in the flowchart or block diagrams may represent a module, segment, or portion of instructions, which comprises one or more executable instructions for implementing the specified logical function(s). In some alternative implementations, the functions noted in the blocks may occur out of the order noted in the Figures. For example, two blocks shown in succession may, in fact, be executed substantially concurrently, or the blocks may sometimes be executed in the reverse order, depending upon the functionality involved. It will also be noted that each block of the block diagrams and/or flowchart illustration, and combinations of blocks in the block diagrams and/or flowchart illustration, can be implemented by special purpose hardware-based systems that perform the specified functions or acts or carry out combinations of special purpose hardware and computer instructions.

The invention claimed is:

1. A method for predicting drug-disease interactions, the method comprising:
    a computer generating a knowledge graph based on ingesting information detailing one or more drugs and one or more diseases;
    the computer identifying one or more drug similarity measures between at least two of the one or more drugs based on the knowledge graph, wherein the one or more drug similarity measures include chemical-protein interactome profile and measures selected from the group comprising chemical structure, drug target, mechanism of action, anatomical therapeutic chemical, metabolizing enzyme, medical subject headings category, side effect, physiological effect, and pathway;
    the computer identifying one or more disease similarity measures between at least two of the one or more diseases based on the knowledge graph, wherein the one or more disease similarity measures include disease pathology and measures selected from the group comprising semantic, disease ontology, disease gene, disease phenotype, disease symptom, disease comorbidity, disease morphology, application independent, domain specific, process based, molecular, and cellular;
    the computer identifying one or more interactions between the one or more drugs and the one or more diseases;
    the computer building one or more drug-disease pair feature vectors based on one or more similarity measures between the one or more interactions, the one or more drug similarity measures, and the one or more disease similarity measures, the one or more similarity measures selected from a group consisting of a max, a mean over positive pairs, a standard deviation over positive pairs, a max Z value, and a mean over all pairs;
    the computer training one or more logistic regression models, wherein the one or more interactions are used as training data, and wherein the one or more drug-disease pair feature vectors are used as variables; and
    the computer applying the one or more logistic regression models in order to calculate a first probability indicating whether a first drug of the one or more drugs will interact with a first disease of the one or more diseases.

2. The method of claim 1, further comprising:
    based on determining that the first probability exceeds a threshold, the computer identifying a second drug having a same intended result of the first drug; and
    the computer determining a second probability indicating whether the second drug will interact with the first disease.

3. The method of claim 1, further comprising:
    utilizing the first probability in a causality assessment.

4. A computer program product for predicting drug-disease interactions, the computer program product comprising:
    one or more computer-readable storage media and program instructions stored on the one or more computer-readable storage media, the program instructions comprising:
    program instructions to generate a knowledge graph based on ingesting information detailing one or more drugs and one or more diseases;
    program instructions to identify one or more drug similarity measures between at least two of the one or more drugs based on the knowledge graph, wherein the one or more drug similarity measures include chemical-protein interactome profile and measures selected from the group comprising chemical structure, drug target, mechanism of action, anatomical therapeutic chemical, metabolizing enzyme, medical subject headings category, side effect, physiological effect, and pathway;
    program instructions to identify one or more disease similarity measures between at least two of the one or more diseases based on the knowledge graph, wherein the one or more disease similarity measures include disease pathology and measures selected from the group comprising semantic, disease ontology, disease gene, disease phenotype, disease symptom, disease comorbidity, disease morphology, application independent, domain specific, process based, molecular, and cellular;
    program instructions to identify one or more interactions between the one or more drugs and the one or more diseases;
    program instructions to build one or more drug-disease pair feature vectors based on one or more similarity measures between the one or more interactions, the one or more drug similarity measures, and the one or more disease similarity measures, the one or more similarity measures selected from a group consisting of a max, a mean over positive pairs, a standard deviation over positive pairs, a max Z value, and a mean over all pairs;
    program instructions to train one or more logistic regression models, wherein the one or more interactions are used as training data, and wherein the one or more drug-disease pair feature vectors are used as variables; and
    program instructions to apply the one or more logistic regression models in order to calculate a first probability indicating whether a first drug of the one or more drugs will interact with a first disease of the one or more diseases.

5. The computer program product of claim 4, further comprising:
based on determining that the first probability exceeds a threshold, program instructions to identify a second drug having a same intended result of the first drug; and
program instructions to determine a second probability indicating whether the second drug will interact with the first disease.

6. The computer program product of claim 4, further comprising:
program instructions to utilize the first probability in a causality assessment.

7. A computer system for predicting drug-disease interactions, the computer system comprising:
one or more computer processors, one or more computer-readable storage media, and program instructions stored on one or more of the computer-readable storage media for execution by at least one of the one or more processors, the program instructions comprising:
program instructions to generate a knowledge graph based on ingesting information detailing one or more drugs and one or more diseases;
program instructions to identify one or more drug similarity measures between at least two of the one or more drugs based on the knowledge graph, wherein the one or more drug similarity measures include chemical-protein interactome profile and measures selected from the group comprising chemical structure, drug target, mechanism of action, anatomical therapeutic chemical, metabolizing enzyme, medical subject headings category, side effect, physiological effect, and pathway;
program instructions to identify one or more disease similarity measures between at least two of the one or more diseases based on the knowledge graph, wherein the one or more disease similarity measures include disease pathology and measures selected from the group comprising semantic, disease ontology, disease gene, disease phenotype, disease symptom, disease comorbidity, disease morphology, application independent, domain specific, process based, molecular, and cellular;
program instructions to identify one or more interactions between the one or more drugs and the one or more diseases;
program instructions to build one or more drug-disease pair feature vectors based on one or more similarity measures between the one or more interactions, the one or more drug similarity measures, and the one or more disease similarity measures, the one or more similarity measures selected from a group consisting of a max, a mean over positive pairs, a standard deviation over positive pairs, a max Z value, and a mean over all pairs;
program instructions to train one or more logistic regression models, wherein the one or more interactions are used as training data, and wherein the one or more drug-disease pair feature vectors are used as variables; and
program instructions to apply the one or more logistic regression models in order to calculate a first probability indicating whether a first drug of the one or more drugs will interact with a first disease of the one or more diseases.

8. The computer system of claim 7, further comprising:
based on determining that the first probability exceeds a threshold, program instructions to identify a second drug having a same intended result of the first drug; and
program instructions to determine a second probability indicating whether the second drug will interact with the first disease.

* * * * *